United States Patent
Nelson et al.

(10) Patent No.: US 10,279,533 B1
(45) Date of Patent: May 7, 2019

(54) METHOD AND APPARATUS FOR FABRICATING BENT MICRONEEDLES FOR USE AS MICRO-SUTURES IN A WOUND CLOSURE DEVICE

(71) Applicant: 10X Technology, LLC, Libertyville, IL (US)

(72) Inventors: John C. Nelson, The Sea Ranch, CA (US); Robert M. Pricone, Libertyville, IL (US); Gregory D. Shields, Round Lake Beach, IL (US); William T. Nelson, Genoa City, WI (US)

( * ) Notice: Subject to any disclaimer, the term of this patent is extended or adjusted under 35 U.S.C. 154(b) by 339 days.

(21) Appl. No.: 14/978,797

(22) Filed: Dec. 22, 2015

Related U.S. Application Data (60) Provisional application No. 62/095,267, filed on Dec. 22, 2014.

(51) Int. Cl.
   *B29C 53/02* (2006.01)
   *A61B 17/08* (2006.01)
   (Continued)

(52) U.S. Cl.
   CPC ............ *B29C 53/02* (2013.01); *A61B 17/085* (2013.01); *A61B 2017/00526* (2013.01);
   (Continued)

(58) Field of Classification Search
   CPC ....... B29C 53/02; B29C 59/00; A61B 17/085; A61B 2017/00526; A61B 17/08; A61B 17/04; B29K 2033/12; B29K 2995/0077; B29K 2033/0077; B29L 2031/753; B29L 2031/756; A61M 2037/0023;
   (Continued)

(56) References Cited

U.S. PATENT DOCUMENTS

| | | | |
|---|---|---|---|
| 2011/0046669 A1* | 2/2011 | Goraltchouk | A61B 17/06166 606/228 |
| 2015/0305739 A1* | 10/2015 | Rolandi | A61B 17/08 606/221 |
| 2015/0352777 A1* | 12/2015 | DeSimone | A61B 5/150022 106/287.24 |

FOREIGN PATENT DOCUMENTS

WO   2010140760 A2   12/2010

OTHER PUBLICATIONS

Poly(methyl methacrylate)—Wikipedia_posted on Jul. 29, 2014 (Year: 2014).*

* cited by examiner

*Primary Examiner* — Matthew J Daniels
*Assistant Examiner* — Yunju Kim
(74) *Attorney, Agent, or Firm* — Medley, Behrens & Lewis, LLC (57) ABSTRACT

A method is provided for forming at least one curved polymeric microneedle, wherein the microneedle includes a base portion and an elongated body portion terminating in a sharp tip, said elongated body portion comprising a lower portion that is 15% to 25% of the height of the microneedle, said elongated body portion being connected to said base layer. The method comprises: heating an array comprising said base layer and at least a segment of said elongated body portion; passing the heated array against a fixed member to bend the microneedles; and allowing the bent, heated array to be cooled. The heat applied to the base layer and elongated body portion is sufficient to cause the heated microneedle to be at or above the glass transition temperature of the polymer of the microneedle, but below a temperature that would cause the lower portion to bend during the passing step.

20 Claims, 4 Drawing Sheets

(51) Int. Cl.
*A61B 17/00* (2006.01)
*B29K 33/00* (2006.01)
*B29L 31/00* (2006.01)

(52) U.S. Cl.
CPC .. *B29K 2033/12* (2013.01); *B29K 2995/0077* (2013.01); *B29L 2031/753* (2013.01); *B29L 2031/756* (2013.01)

(58) Field of Classification Search
CPC .. A61M 2037/0046; A61M 2037/0053; A61M 37/00
USPC .......................................................... 264/322
See application file for complete search history.

METHOD AND APPARATUS FOR FABRICATING BENT MICRONEEDLES FOR USE AS MICRO-SUTURES IN A WOUND CLOSURE DEVICE

CROSS-REFERENCE TO RELATED APPLICATIONS

This application claims the benefit of priority of U.S. provisional application 62/095,267, filed on Dec. 22, 2014, titled Method and Apparatus for Fabricating Bent Microneedles for use as Micro-Sutures in a Wound Closure Device. This prior application is incorporated herein by reference.

FIELD

This disclosure relates generally to a method and apparatus for providing the necessary shapes of microstructured needles in a polymeric device used for wound healing in lieu of traditional types of suturing or stapling.

BACKGROUND

Compositions and devices for wound closures are well known. The most common being simple adhesive based strips, or bandages, such as BAND-AIDS®, or for more specialized purposes, sutures or staples. The application of sutures or staples typically requires a trained specialist and the procedures are invasive and painful and may require anesthetic. Moreover, those procedures often leave unsightly scars from secondary insertion holes and spacing and depth variation. Also, frequently follow-up visits to doctor or by other trained professional for removal is required. Simple bandages or BAND-AIDS often are not adequate to close and hold more severe or deeper wounds; and pulling off the bandage is painful.

Others have invented a wound closure device which comprises a series or array of microstructured needles affixed to a backing device. Using two spaced arrays, they may be positioned on opposite sides of the wound needing closure. These devices can be easily applied and removed with little pain, as no adhesive is used and the microneedles are inserted only to a depth of the upper epidermis that essentially is devoid of the pain-nerve endings.

The optimum length, sharpness and height of the microneedles has been a result of extensive study and it has been determined that microneedles that are bent (or curved, and for purposes of this application the term "bent" includes a smooth or radiused curve) provide the most desirable structure for both skin penetration and effectively anchoring or holding power over the wound at the stratum corneum. Also for purposes of this application the term micro-needle is all inclusive of various shapes and cross-sections of the needle, such as conical, pyramidal, blade, rectangle, or other variations, each ending with an elongated sharper end referenced as the tip which is intended to enter the skin adjacent the wound to be closed.

The density of the microneedles may be predetermined and may vary depending upon the size of the device and the wound to be closed, much as bandages vary in size and the location on the body where they are to be applied. For example the density may be 1 microneedle/cm$^2$ to 1 microneedle/10 cm$^2$. The pitch between adjacent microneedles may be from 30 µm to 1 cm, wherein pitch is defined as the distance between needles, center point to center point.

Because of the very small configuration of the microneedles in terms of reduced cross section from the base to the sharp tip, and the relative rigidity required to assure stability and anchoring of the device when installed over a wound, it has been very difficult to provide an economic and useful method for producing these devices having bent microneedles in an efficient and accurate manner.

The preferred materials for the device must be FDA approved polymers; one of the most useful for this purpose is PMMA. Others have tried to injection mold hooks using PMMA for Velcro® type hook and loop fasteners, but found that the PMMA was too stiff to be easily removed from the mold and still retain the necessary curvature.

While one may achieve a bent shape by possible reheating the hook, or forming the bent shape as the hook is formed, the high temperature necessary for bending needed at the middle of the needle could affect the sharpness of the tip.

WO 2010/140760 A2 describes using a curved substrate to attempt to angle micro-needles inward. But in order to replicate needle arrays from a mold, undercuts cannot be readily achieved.

SUMMARY

The method and apparatus disclosed herein uses a post needle forming process to impart the controlled curve configuration of each needle in the array.

In an embodiment, a method of forming at least one curved polymeric microneedle having an uncurved height no greater than 3 mm and a curved height in the range of 60 to 80% of the uncurved height is provided. The microneedle includes a base portion and an elongated body portion terminating in a sharp tip, and attached to a base layer, said elongated body portion comprising a lower portion that is 15% to 25% of the length of the uncurved height of the microneedle, the microneedle being fixedly connected to said base layer, comprising the steps of: heating at least a segment of said elongated body portion of the microneedle having an uncurved height no greater than 3 mm and attached to said base layer having a thickness in the range of between 25 µm and 250 µm, thereby forming a heated microneedle; passing the heated microneedle against a fixed member that causes said body portion to be bent to the curved height that is in the range of 60 to 80% of the uncurved height, thereby forming a bent, heated microneedle; and allowing said bent, heated microneedle to be cooled while in the bent condition. The heat applied to the elongated body portion is sufficient to cause the heated microneedle to be at or above the glass transition temperature of a polymer comprising the microneedle but below a temperature of the polymer that would cause the lower portion to bend during the passing step.

In an embodiment, a method of forming at least one curved polymeric microneedle having an uncurved height no greater than 3 mm and a curved height in the range of 60 to 80% of the uncurved height is provided. The microneedle includes a base portion and an elongated body portion terminating in a sharp tip, and attached to a base layer, said elongated body portion comprising a lower portion that is 15% to 25% of the length of the uncurved height of the microneedle, comprising the steps of: heating an array comprising said base layer and at least a segment of said elongated body portion, thereby forming a heated array; passing said heated array against a fixed member that causes each said body portion to be bent to a curved height, thereby forming a bent, heated array; and allowing said bent, heated array to be cooled while in the bent condition. The heat applied to the base layer and elongated body portion is sufficient to cause the heated microneedle to be at or above the glass transition temperature of a polymer comprising the microneedle, but below a temperature of the polymer that would cause the lower portion to bend during the passing step.

In an embodiment, an apparatus for bending an array of uncurved polymeric microneedles to a predetermined height, which is 60 to 80% of the uncurved height, is provided. The apparatus includes: means for feeding an array of straight microneedles past a heating station, the microneedles comprising a base portion and an elongated body portion, terminating in a sharp tip, said elongated body portion comprising a lower portion that is 15% to 25% of the length of the uncurved height of the microneedle; said heating station comprising means for applying heat primarily to said base portion and a segment of said elongated body portion; means for moving said heated array of microneedles past a fixed member, the fixed member being spaced such that a gap distance between a bottom surface of the array and said fixed member is at a predetermined height, which causes said microneedles to be bent to the predetermined height, thereby forming a bent array, and passing said bent array to a cooling area, while said microneedles in the array are in a bent position. The heat applied to the elongated body portion is sufficient to cause the elongated body portion to be at or above the glass transition temperature of a polymer comprising the microneedles but below a temperature of the polymer that would cause the lower portion to bend when moving said heated array of microneedles past the fixed member.

DETAILED DESCRIPTION

The present disclosure provides methods for forming an array of bent polymeric microneedles having the requisite physical properties, including the necessary sharpness to facilitate easy penetration of the skin. In addition to holding the wound closed, the microneedles may be provided with a drug delivery or antibiotic coating to enhance healing and minimize infection.

In an embodiment, straight microneedles are heated and then bent to a certain angle and then cooled to retain the proper angle while preserving sharpness of the needle tip.

In another embodiment, the bent microneedles are formed from a polymer having an elastic modulus that both permits bending of straight microneedles but that will also hold a wound closed without the microneedles breaking. Elastic modulus may be determined by ASTM E2769-15.

In another embodiment, one or more arrays of straight microneedles are formed in a web or sheet of thermoplastic material. The arrays are then heated in specific zones to achieve slightly softening temperature in the mid-depth/height of the needle while keeping the tip zone of the needle at a cooler temperature so the tips do not lose their sharpness. Once the temperature zones are established, the web or sheet is passed through a controlled gap to bend the needles to the desired angle. The needles are then cooled to set the thermoplastic shape to the desired bent needle geometry.

Figure 1:
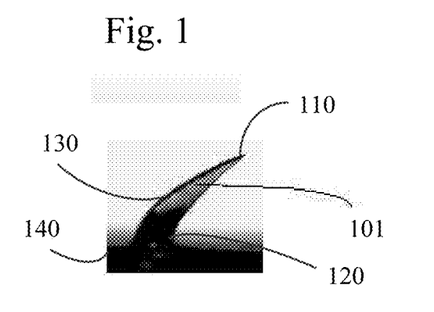
FIG. 1 is a photograph of a greatly enlarged bent microneedle formed in accord with the present invention.

FIG. 1 is an enlarged photograph of a single microneedle 101 that was formed in accordance with one method disclosed herein. In this case, a microneedle 101 has a base portion 120 and an elongated body portion 130 ending in a sharp tip 110 of 30 μm radius or less, such as, for example, 1 μm to 20 μm, or 2 μm to 10 μm. The microneedle 101 is formed of PMMA with a height of 500 μm to 2,000 μm from the tip 110 to the base portion of the needle 120 where the microneedle intersects with the base layer 140 with 1,000 μm tall being preferred for a wound or surgical incision of 3 cm in length and with a base portion 120 or layer 140 that is 125 μm thick and an elastic modulus of 2.4 to 1.6 GPa with 1.86 GPa being preferred for a 1,000 μm tall microneedle and bent to a height of about 700 μm, plus or minus 10%, as measured from the tip of the microneedle to the top of the base layer as depicted. In an embodiment, the base layer may range from 25 μm and 250 μm, such as, for example, 75 μm to 200 μm, or 100 μm to 150 μm.

Figure 2:
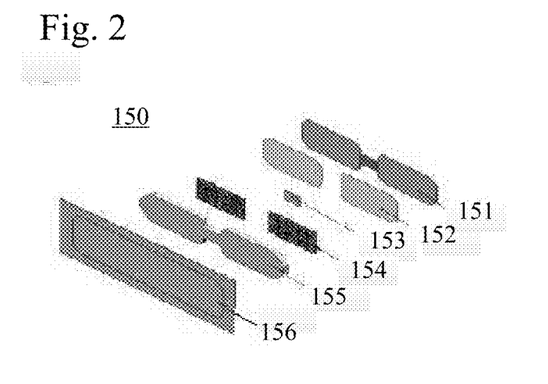
FIG. 2 is an exploded view of one form of device that usefully uses arrays of bent microneedles, as would be assembled for packing prior to insertion over a wound.

FIG. 2 depicts an exploded view of how arrays of bent microneedles can be assembled as part of a package for use in wound closure. FIG. 2 is for exemplary purposes only. The device 150 may include the following layers: a base 151 (or what will be the top layer of the device 150 when installed); an adhesive layer 152; a hydrogel or other appropriate material 153 that directly overlies the wound; a pair of microneedle arrays 154; a release liner 155 that overlays the arrays 154 and that would be removed prior to application of the device 150 over the wound, and a suitable removable packaging pouch 156 for carrying the device 150. The oppositely directed inwardly curving needles on the arrays 154 will penetrate and mechanically hook the skin and tightly adhere under the tension of the backing layer 151. In an embodiment, these layers are joined in the melt state to bond them together.

In each of the needle arrays 154, there may be as few as 12 microneedles in an array, spaced about 3 mm from each other in array on the order of 15 mm×15 mm. The array of this size may have as many as 36 needles and spaced 2 mm apart. This tight spacing and low height requires a precise bending of the needles to accomplish their intended purpose. It has been found that using the present processes disclosed one can achieve an accuracy rate of about 95% within +/−5% tolerance. In an embodiment, the microneedles may have a density on the needle arrays of 0.053 needles/mm$^2$ to 0.16 needles/mm$^2$, such as 0.08 to 0.14 needles/mm$^2$ or 0.1 to 0.12 needles/mm$^2$.

When used in devices 150 of different sizes, the number, height and spacing of the needles may vary from device to device. If devices are used over larger wounds for example, taller needles may be needed to assure wound closure. This would be particularly true where a device is used in an emergency/trauma situation where sutures and staples are unavailable and where blood may cause ordinary bandages to slip. For example, needles with up to 3 mm height in may be used in such an embodiment, such as 0.1 mm to 2 mm, or 0.5 mm to 1 mm.

Figure 3:
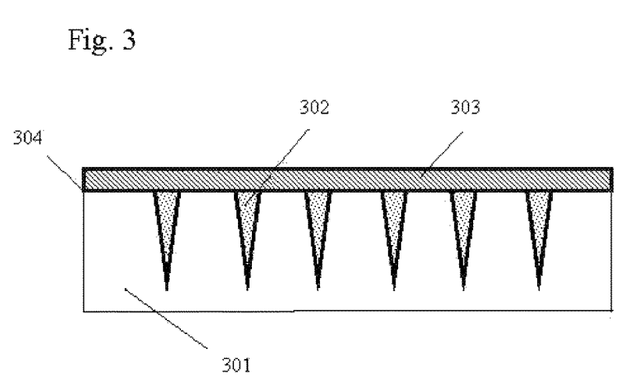
FIG. 3 is an enlarged view of a mold demonstrating how two different polymers are used to provide microneedles of one polymer and a backing layer of a second polymer.

FIG. 3 is an enlarged view of a microneedle mold 301. The mold is filled with a first PMMA polymer 302 as a powder with the excess wiped from the surface 304. A second, and different PMMA polymer film 303 is placed on the top of the mold 301. This polymer film 303 acts as a backing for the microneedles. Under the heat and pressure of the embossing process, the powdered PMMA polymer 302 melts and fuses to the backing layer 303. After cooling, the microneedles and backing layer are removed as a single sheet having the microneedles as one polymer and the backing layer as a second polymer. In an embodiment, the first and second polymer may be the same.

Figure 4:
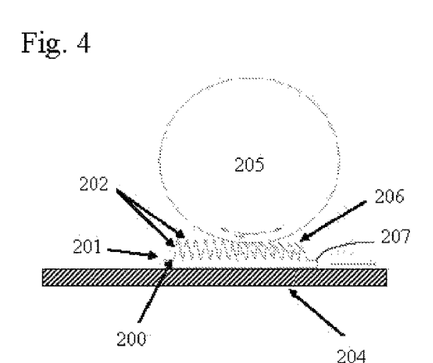
FIG. 4 is a side elevation view of an array of straight microneedles after being heated on a hot plate and then bent by a fixed roller.

FIG. 4 is a side elevational view of one form of apparatus for use in the present method. In this case a sheet or film having an array 200 of straight microneedles 201 is fed to the right in the direction of the arrow between a hot plate 204 and a shear roller 205. The microneedles elongated body portions 201 may be 1,000 μm tall when straight or the ranges disclosed herein, having tips 202 that will have less than a 30 μm radius, as disclosed above. One useful polymer to form the microneedles is Arkema DR100 PMMA with an elastic modulus of 1.86 GPa, a Tg of 80° C., a Vicat Softening point of 86° C. and a melt flow index of 1.0 grams in 10 minutes. The base layer 207 is also Arkema DR100 with a 125 μm thickness supporting the microneedles.

It has also been determined that using two different PMMA polymers, one to form the microneedles and one to form the base layer, each with a different moduli, such as Evonik OFO26 PMMA with an elastic modulus of 2.7 GPa forming the microneedles and Arkema DR100 PMMA with an elastic modulus of 1.86 GPa forming the base layer can be achieved by thermally bonding the micro-needle body portion and base layer of PMMA having the desired attributes. In this embodiment, the elastic modulus of the base layer is lower than the elastic modulus of the microneedles. The relatively thin and soft base layer 207 is intended to be flexible enough to allow contour around extremities. In this case, the hot plate 204 is pre-heated to 130 degrees C., which is slightly above the glass transition temperature of the needle polymer. By calibrating the thickness of the base layer 207 and the height of the microneedles 201, the plastic nature stays within a narrow zone and does not allow the tip area to be at the glass transition temperature, thus retaining its shape. For this height of microneedle 201, the gap between the shear roller 205 and the hot plate 204 was set at 0.73 mm, the diameter of the roller 205 is 9.5 mm and is fixed so it does not rotate. When the microneedles 201 are moved through the gap between the hot plate 204 and the roller 205, the body of the microneedle 201 bends so that the tips 202 bend as indicated at 206. The bent needles are then cooled to permanently fix their shape in the desired configuration. Changes in the gap will affect the degree of bend; it also will depend on the height of the original needles and the polymers being used.

Precision temperature control is useful and several methods of shear have been used to create the bending moments. Because the polymer is heated to only slightly above the glass transition temperature, such as, for example from 0.1 to 10 degrees, or 1 to 5 degrees above the glass transition temperature, the needles do not sag but rather obey Hooke's law and are linearly elastic. This keeps the hook shape from deforming plastically. The strain or deformation of an elastic object or material is proportional to the force applied to it. Typically, the rollers of the various embodiments discussed herein will accurately bend the needles if the temperature is kept within a determined range. This range may vary depending upon the polymer, but for the PMMA discussed herein the range is 95 degrees C. to 130 degrees C.

Figure 5:
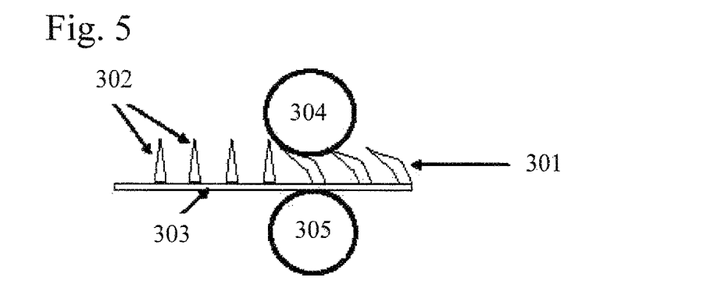
FIG. 5 is a side elevation view of an array of straight microneedles that have been pre-heated and then are being bent by two fixed rollers.

FIG. 5 is a side elevational view of an array 301 of straight microneedles 302, having a height of 1,000 μm tall, or in a range as described above, having tips with a 30 μm radius, or in a range as described above. The same Arkema PMMA polymer with the elastic modulus of 1.86 GPa is used. The backing layer 303 holding the microneedles is 125 μm thick PMMA with an elastic modulus of 1.86 GPa. In this apparatus, the arrays were pre-heated with a hot plate or by passing the film or sheet through an oven (not shown) while positioned on a higher melting point polymer such as PET or Kapton. The higher melting point polymer allows the needles and backing film to be preheated to the softening point and moved through the rollers 304 and 305 without stretching the array 301 provided all the tension is on the higher melting point polymer and pulled through the gap between the rollers 304, 305. In this embodiment, the temperature at the upper portion of the elongated body portion of the microneedles, e.g. the upper 80%, or 75% to 85% of the uncurved height, is at or above the glass transition temperature of the polymer, e.g. 105 degrees C. to allow the microneedles to bend without losing their shape or sharpness. The lower portion, e.g. the lower 20%, such as 15% to 25%, or 17 to 22% of the uncurved height of the elongated body portion is heated to a temperature above the glass transition temperature of the polymer that comprises it, but is not so high as to cause the lower portion to bend when bending the upper portion, such as by moving said heated array of microneedles past a fixed member. The gap between the rollers 304 and 305 was set at 0.73 mm.

Figure 6:
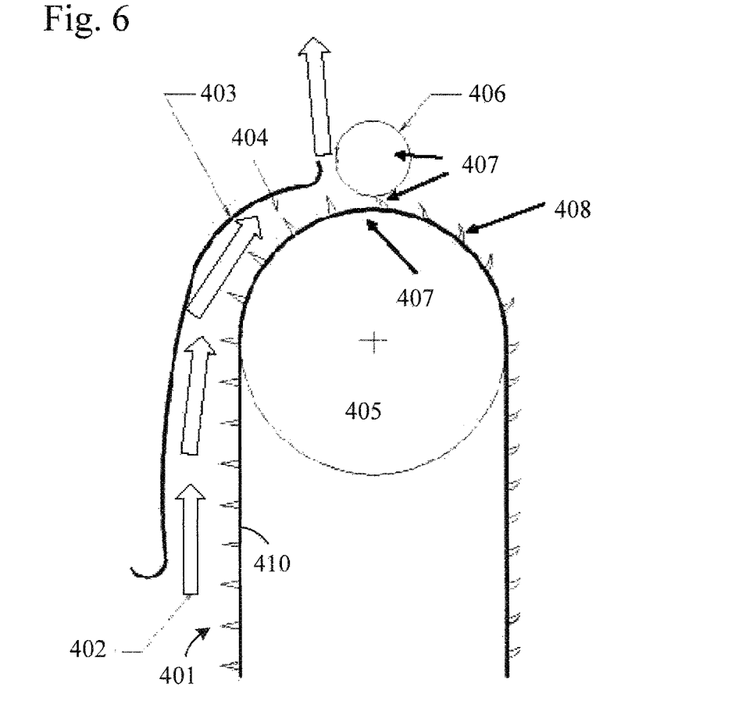
FIG. 6 is a side elevation view of apparatus showing how a continuous array of straight microneedles is being heated by a stream of hot air and then being bent by a fixed roller while the base of the micro-needles is being kept at cooler temperature.

FIG. 6 is a side elevational view of an array of straight microneedles 404 of the same range in height and radius and having similar properties as described in the other embodiments. In this case, a continuous roll of straight polymeric needles 401 is being wrapped around a metal cooling roll 405. The cooling roll keeps the base of the array below the glass transition temperature so the microneedles don't lean at the base, but rather bend uniformly along an arc. Provided the base remains cooler while the needles are at the right temperature, the desired bend will occur. An airflow 402 of 130 degrees C. is directed by a shroud 403 heating the polymeric needles 401 at the correct zone while the cooling roll 405 maintains the base layer 410 at a lower temperature. When the microneedles 404 reach the shear roll 406, the gap 407 between the shear roll 406 and the cooling roll 405 determines the amount and degree of bend 408. In this case, the bend is measured from the tip of the needles to the base below the needles. For 1,000 μm tall needles the desired dimension is typically 700 μm.

The dimension of the gap will be sized according to the height of the microneedles as straight and as bent.

Figure 7:
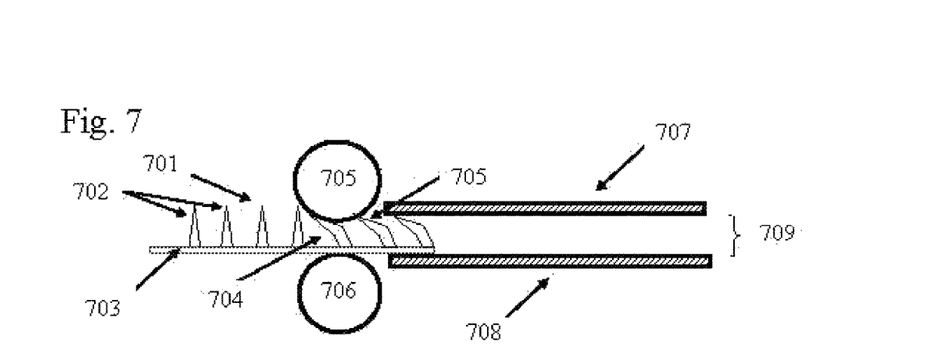
FIG. 7 is a side elevation view of an array of straight microneedles after being heated on a hot plate and then bent by a fixed roller; then being held in place by two plates while being cooled.

FIG. 7 is a side elevational view of an array 701 of straight microneedles 702, 1000 μm tall having tips with less than 30 μm radius. In this embodiment, the same PMMA polymer with the elastic modulus of 1.86 GPa is used for the microneedles and backing layer 703. The backing layer 703 holding the microneedles is 125 μm thick. The gap 704 between the rollers 705 and 706 was set at 0.73 mm. After passing through the rollers the pre-bent microneedles 702 then pass between two plates 707 and 708 that are spaced at a gap 709 of 0.88 mm holding the microneedles in place until they cool. After cooling, the bent microneedle height is 700 μm+/−10%, as measured from the tip of the microneedle to the top of the base layer.

Figure 8:
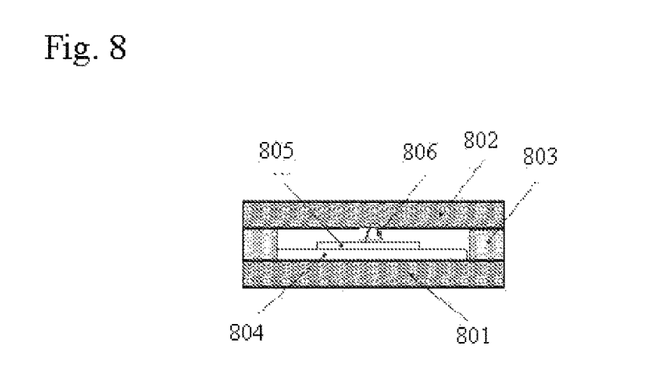
FIG. 8 is a side view of the two plates holding needles while cooling and the spacers between the plates.

FIG. 8 is an elevational view of a microneedle elongated body portion 806 and the backing or base layer 805 passing between two plates 801 and 802 that are spaced 803 to hold the microneedle in the correct position until cooled. The microneedle array is attached to a metal carrier 804 that pulls it through the plates 801, 802 keeping the base layer 805 from stretching during the process. The microneedle array can be held to the plate by vacuum or adhesive tape, not shown.

Thus, there has been disclosed both method and apparatus for forming at least one curved polymeric needle having an uncurved height no greater than 3 mm and a curved height in the range of 60 to 80% of the uncurved height. The method includes the steps of heating a portion of a pre-formed polymeric microneedle having an elongated body portion and a height preferred to be no greater than 3 mm and attached to a polymeric base having a thickness in the range of between 25 μm and 250 μm; causing the heat to be focused on that portion along the height of the microneedle that is below about the top ⅓ of the total height of the microneedle body portion and wherein the heat applied to such portion is sufficient to cause the microneedle polymer to be at or above a glass transition temperature, but below a temperature of the polymer that would cause the lower portion, e.g., 20%, to bend when bending the upper portion (e.g. 80%) such as by moving said heated array of microneedles past a fixed member. The specification describes in detail several embodiments of the present invention. Other modifications and variations will, under the doctrine of equivalents, come within the scope of the appended claims. For example, microneedles having somewhat different geometries and/or different dimensions are considered equivalent structures. Different thermoplastic materials may affect heating temperature as well as process speed. Further, different material densities and thicknesses may also affect the apparatus and process. There is no desire or intention here to limit in any way the application of the doctrine of equivalents. The terms "a," "an," or "the," mean one or more, unless the context clearly indicates to the contrary.

What is claimed is:

1. A method of forming at least one curved polymeric microneedle on a base layer; the microneedle having an uncurved height no greater than 3 mm and a curved height in the range of 60 to 80% of the uncurved height, wherein the microneedle includes a base portion where the microneedle intersects with and is attached to the base layer and an elongated body portion terminating in a sharp tip, said elongated body portion comprising a lower portion that is 15% to 25% of the length of the uncurved height of the microneedle, comprising the steps of:

heating at least a segment of said elongated body portion of the microneedle having an uncurved height no greater than 3 mm and attached to said base layer having a thickness in the range of between 25 μm and 250 μm, thereby forming a heated microneedle;

cooling the base portion of the microneedle; and passing the heated microneedle against a fixed member that causes said body portion to be bent to the curved height that is in the range of 60 to 80% of the uncurved height, thereby forming a bent, heated microneedle; and allowing said bent, heated microneedle to be further cooled while in the bent condition;

wherein the heat applied to the elongated body portion is sufficient to cause the heated microneedle to be at or above the glass transition temperature of a polymer comprising the microneedle but below a temperature of the polymer that would cause the lower portion to bend during the passing step.

2. The method of claim 1, wherein said at least one curved polymeric microneedle is an array of microneedles having a pitch of 30 μm to 1 cm.

3. The method of claim 1, wherein said elongated body portion may have a shape selected from the group consisting of: a pyramid, rectangle, cone, or blade.

4. The method of claim 1, wherein heat is applied in the range of 95 degrees C. to 130 degrees C.

5. The method of claim 1, wherein the microneedle comprises a PMMA polymer having an elastic modulus of 1.86 GPa and wherein heat is applied at about 130 degree C.

6. The method of claim 1, wherein the microneedle comprises a polymer having an elastic modulus of 2.4 to 1.6 GPa.

7. The method of claim 1, wherein the microneedle comprises a first polymer and the base layer comprises a second polymer; and the first and second polymers are different.

8. The method of claim 7, wherein the elastic modulus of the second polymer is lower than the elastic modulus of the first polymer.

9. The method of claim 2, wherein the array comprises a film coupled to the microneedles that is coupled to carrier means to minimize stretching of the film and minimize distortion of the density of the microneedles on the array, as the array is passed through the heating station, fixed member, and cooling area.

10. The method of claim 1, wherein an upper portion is the upper 80% of the uncurved height of the elongated body portion.

11. The method of claim 1, wherein the lower portion is the lower 25% of the uncurved height of the elongated body portion.

12. The method of claim 1, further comprising cooling the base layer with a cooling roll to keep the base portion below its glass transition temperature.

13. The method of claim 1, wherein the microneedle does not tilt at the base portion of the microneedle.

14. The method of claim 1, wherein the at least one curved polymeric microneedle is in an array of microneedles having a density of 0.053 needles/$mm^2$ to 0.16 needles/$mm^2$.

15. A method of forming at least one curved polymeric microneedle on a base layer; the microneedle having an uncurved height no greater than 3 mm and a curved height in the range of 60 to 80% of the uncurved height, wherein the microneedle includes a base portion attached to the base layer and an elongated body portion terminating in a sharp tip, and attached to a base layer, said elongated body portion comprising a lower portion that is 15% to 25% of the length of the uncurved height of the microneedle, comprising the steps of:

heating an array comprising said base layer and at least a segment of said elongated body portion of the at least one microneedle, thereby forming a heated array;

cooling the base portion of the microneedle; and passing said heated array against a fixed member that causes each said body portion to be bent to a curved height, thereby forming a bent, heated array; and allowing said bent, heated array to be further cooled while in the bent condition;

wherein the heat applied to the base layer and elongated body portion is sufficient to cause the heated microneedle to be at or above the glass transition temperature of a polymer comprising the microneedle, but below a temperature of the polymer that would cause the lower portion to bend during the passing step.

16. The method of claim 15, wherein the polymer of the elongated body portion has an elastic modulus of 2.4 to 1.6 GPa.

17. The method of claim 15, wherein the polymer of the elongated body portion comprises a first polymer and the polymer of the base layer comprises a second polymer; and the first and second polymers are different.

18. The method of claim 17, wherein the elastic modulus of the second polymer is lower than the elastic modulus of the first polymer.

19. The method of claim 15, wherein the microneedle does not tilt at the base portion of the microneedle.

20. The method of claim 16, further comprising cooling the base layer with a cooling roll to keep the case portion below its glass transition temperature.

* * * * *

UNITED STATES PATENT AND TRADEMARK OFFICE
CERTIFICATE OF CORRECTION

PATENT NO. : 10,279,533 B1
APPLICATION NO. : 14/978797
DATED : May 7, 2019
INVENTOR(S) : John C. Nelson et al.

Page 1 of 1

It is certified that error appears in the above-identified patent and that said Letters Patent is hereby corrected as shown below:

In the Claims

Claim 20, at Column 9, Line 24 should recite --"claim 1"-- instead of "claim 16"; and Claim 20, at Column 9, Line 25 should recite --"base"-- instead of "case"

Signed and Sealed this
Eighteenth Day of June, 2019

Andrei Iancu
*Director of the United States Patent and Trademark Office*